United States Patent
Kawachi et al.

(10) Patent No.: US 7,206,631 B2
(45) Date of Patent: Apr. 17, 2007

(54) SLEEPINESS LEVEL DETECTION DEVICE

(75) Inventors: Taiji Kawachi, Kariya (JP); Tsuyoshi Nakagawa, Aichi-gun (JP); Akiko Ito, Nagoya (JP); Takeshi Yoshinori, Okazaki (JP)

(73) Assignee: Denso Corporation, Kariya (JP)

( * ) Notice: Subject to any disclaimer, the term of this patent is extended or adjusted under 35 U.S.C. 154(b) by 386 days.

(21) Appl. No.: 10/852,955

(22) Filed: May 25, 2004

(65) Prior Publication Data
US 2004/0243013 A1    Dec. 2, 2004

(30) Foreign Application Priority Data
May 27, 2003 (JP) .............................. 2003-149630

(51) Int. Cl.
*A61B 5/04* (2006.01)

(52) U.S. Cl. ....................................... 600/519; 600/509
(58) Field of Classification Search .................... None
See application file for complete search history.

(56) References Cited

U.S. PATENT DOCUMENTS

| | | | |
|---|---|---|---|
| 4,569,536 A | | 2/1986 | Tsuge et al. |
| 4,832,038 A | | 5/1989 | Arai et al. |
| 5,769,085 A | | 6/1998 | Kawakami et al. |
| 5,813,993 A | * | 9/1998 | Kaplan et al. ............... 600/544 |
| 5,917,415 A | | 6/1999 | Atlas |
| 6,070,098 A | * | 5/2000 | Moore-Ede et al. ......... 600/544 |
| 6,506,153 B1 | | 1/2003 | Littek et al. |
| 6,678,547 B2 | * | 1/2004 | Carlson et al. ............. 600/515 |
| 6,960,168 B2 | * | 11/2005 | Yanagidaira et al. ....... 600/300 |
| 2003/0199943 A1 | * | 10/2003 | Katz et al. .................... 607/48 |

FOREIGN PATENT DOCUMENTS

| | | |
|---|---|---|
| GB | 2 375 645 | 11/2002 |
| JP | 7-143972 | 6/1995 |
| JP | 11-314534 | 11/1999 |
| JP | 11-321375 | 11/1999 |

OTHER PUBLICATIONS

Examination Report from corresponding CN patent application No. 200410044788.2 issued Sep. 15, 2006.

* cited by examiner

*Primary Examiner*—Carl Layno
(74) *Attorney, Agent, or Firm*—Harness, Dickey & Pierce, PLC (57) ABSTRACT

A sleepiness level detection device detects a heartbeat signal when a time equal to or longer than T1 and equal to or shorter than T2 has elapsed since the start of driving. The heartbeat signal is subjected to FFT processing to obtain a spectrum signal. By use of a peak frequency of the spectrum signal, a driver conscious-state peak frequency is estimated. A consciousness level index band $\alpha$ is set with respect to the conscious-state peak frequency. A sleepiness level index band $\beta$ is set with respect to a frequency, which is calculated by multiplying the conscious-state peak frequency by a predetermined ratio (65 to 90%). A sleepiness level evaluation parameter Sp ($=\beta p/(\alpha p+\beta p)$) for indicating the sleepiness level of the driver is calculated with the use of the strength $\alpha p$ and $\beta p$ of spectrum signals.

10 Claims, 7 Drawing Sheets

EXAMPLE OF WAVEFORM OF
GENERAL HEARTBEAT SIGNAL

SLEEPINESS LEVEL DETECTION DEVICE

CROSS REFERENCE TO RELATED APPLICATIONS

This application is based upon, claims the benefit of priority of, and incorporates by reference Japanese Patent Application No. 2003-149630 filed May 27, 2003.

BACKGROUND OF THE INVENTION

1. Field of the Invention

The present invention relates to a sleepiness level detection device for detecting the sleepiness level of a test subject who operates equipment such as a vehicle and the like.

2. Description of the Related Art

Conventionally, as disclosed in Japanese Patent Laid-Open Publication No. Sho 60-15240 (1985), a device calculates the heart rate of the driver of a vehicle on the basis of, for example, the electric potential difference between electrodes provided in a steering wheel of the vehicle, in order to judge a state of tension or dozing of the driver on the basis of the heart rate. To be more specific, the device detects R-waves, having a high pulse-height value, and the like of heart potential, and converts time intervals of occurrence of the R-waves into the driver's heart rate in a heart rate conversion circuit. The heart rate decreases during sleep, and increases during tension, which is experienced during an awake state. Thus, the heart rate converted by the heart rate conversion circuit is compared with a predetermined heart rate range to judge whether the heart rate is abnormally higher or lower than the predetermined heart rate. When the heart rate is not in the predetermined heart rate range, the device issues a warning with an alarm lamp, a buzzer, or the like, and also tightens a seat belt to give a physical warning to the driver.

As described above, the conventional device determines whether the driver is in a normal physical state or in a state of tension or dozing, simply on the basis of whether or not the heart rate is in the predetermined heart rate range. As to the dozing state of the driver of the vehicle, however, the driver does not suddenly fall asleep from a conscious state, but the driver eventually reaches the dozing state after gradual increase in a sleepiness level. In the case of driving the vehicle or other equipment, the driver has less attention and the like even in a state of increasing the sleepiness level, as compared with his/her conscious state. Thus, it is desirable that the state of increasing sleepiness be precisely detected. This is because if the sleepiness level of the driver of a vehicle or an operator of equipment is precisely detected, it is possible to take appropriate measures such as issuing a warning in accordance with the sleepiness level, or restricting the operation of the equipment, and the like.

SUMMARY OF THE INVENTION

Considering the foregoing problems, an object of the present invention is to provide a sleepiness level detection device which can precisely detect the sleepiness level of a test subject.

To achieve the above object, a sleepiness level detection device, according to an aspect of the invention, has a heartbeat signal detection means, calculation means, and an evaluation means. The heartbeat signal detection means detects the heartbeat signal of a test subject. The calculation means carries out frequency analysis on the heartbeat signal to calculate a spectrum signal which indicates the distribution of frequency components included in the heartbeat signal. The evaluation means sets a band having a lower frequency than a conscious-state peak frequency as a sleepiness level index band for indicating a sleepiness level, in the spectrum signal, with respect to the conscious-state peak frequency in a conscious state of the test subject. The evaluation means evaluates the sleepiness level of the test subject on the basis of the strength of the spectrum signal in the sleepiness level index band.

Since the heart rate decreases as the sleepiness of the test subject increases, the frequency components included in the heartbeat signal of the test subject decreases as the sleepiness level of the test subject increases. Thus, the sleepiness level can be quantitatively detected by the frequency components included in the heartbeat signal. Namely, in the spectrum signal, which indicates the distribution of the frequency components included in the heartbeat signal, the band having the lower frequency than the conscious-state peak frequency is set as the sleepiness level index band, with respect to the conscious-state peak frequency in the conscious state of the test subject. When the consciousness level of the test subject is high, the heart rate hardly decreases. In this case, the low frequency component included in the heartbeat signal is slight, and hence the strength of the spectrum signal in the sleepiness degree index band becomes low. As the sleepiness level of the test subject increases, on the other hand, decrease in the heart rate becomes conspicuous, and the low frequency component included in the heartbeat signal increases. Thus, the strength of the spectrum signal in the sleepiness level index band increases. Since the strength of the spectrum signal in the sleepiness level index band is correlated with the sleepiness level, it is possible to precisely evaluate the sleepiness level of the test subject by the strength of the spectrum signal.

According to another aspect of the invention, it is preferable that the calculation means converts the heartbeat signal into a signal, which has peaks only at the largest peak positions of the heartbeat signal, and carries out frequency analysis on the converted signal. A single waveform of the heartbeat signal includes a P-wave, a Q-wave, an R-wave, an S-wave, and a T-wave, each wave shows a peak. Thus, if the heartbeat signal is subjected to direct frequency analysis, a spectrum signal including frequency components of each wave described above is calculated. In the present invention, however, the heart rate in the heartbeat signal per unit of time, in other words, the frequency components ascribable to the heart rate is analyzed, so that the frequency components of each wave described above become a cause of an error. For this reason, the heartbeat signal is converted into the signal having only the largest peaks (generally, the R-waves) of the heartbeat signal, and then the frequency analysis is carried out on the converted signal. Therefore, it is possible to obtain the spectrum signal which precisely indicates the frequency components ascribable to the heart rate.

According to another aspect of the invention, the evaluation means evaluates the sleepiness level of the test subject when the test subject operates predetermined equipment. It is preferable that the peak frequency of the spectrum signal at a time when a predetermined time has elapsed since the test subject starts operating the predetermined equipment is set as the conscious-state peak frequency. Since the heart rate (namely, the heartbeat frequency) in the conscious state differs in individuals, it is not preferable that a fixed frequency is set as the conscious-state peak frequency. Thus, it is necessary to set the conscious-state peak frequency for each test subject. It is apparent from experiments by the inventor of the present application that a spectrum signal, as the result of frequency analysis of a heartbeat signal just after the test subject starts operating a vehicle or the like, has a peak frequency different from the conscious-state peak frequency. This is because the test subject is temporarily in a state different from a usual one, such as in a state of tension and the like. Thus, when a predetermined time has elapsed and the test subject gets used to the operation of the equipment, the peak frequency of the spectrum signal at that time is set as the conscious-state peak frequency. Therefore, it is possible to increase the precision of the set conscious-state peak frequency.

To further increase the precision of the conscious-state peak frequency, according to another aspect of the invention, it is preferable that the conscious-state peak frequency is calculated by averaging peak frequencies of a plurality of spectrum signals. The plurality of spectrum signals are calculated for a predetermined detection time, from a point in time when the predetermined time has elapsed since the test subject starts operating the predetermined equipment. Therefore, it is possible to reduce the effect of noise and the like on the conscious-state peak frequency.

According to another aspect of the invention, it is preferable that the predetermined time is selected in a range from 100 seconds to 500 seconds. This is because, as described above, the effect of tension caused by the start of operation remains just after the start of operation. When an excessively long time period has elapsed, on the other hand, the test subject gets used to the operation and the sleepiness level may increase.

According to another aspect of the invention, it is preferable that the evaluation means sets a band including the conscious-state peak frequency as a consciousness level index band, and evaluates the sleepiness level of the test subject, with the use of the strength of the spectrum signals in the consciousness level index band and the sleepiness level index band. In other words, the strength of the spectrum signal in the consciousness level index band increases, as the consciousness level of the test subject increases. The strength of the spectrum signal in the sleepiness level index band increases, as the sleepiness level of the test subject increases. Thus, comparing both spectrum signals makes it possible to judge which of the consciousness level and the sleepiness level of the test subject is higher. Therefore, it is possible to further precisely evaluate the sleepiness level.

In this case, according to another aspect of the invention, it is preferable that the evaluation means calculates a sleepiness level evaluation parameter. A denominator of the sleepiness level evaluation parameter is the sum of the strength of the spectrum signals in the consciousness and sleepiness level index bands. A numerator of the sleepiness level evaluation parameter is the strength of the spectrum signal in the sleepiness level index band. The sleepiness level evaluation parameter, considering both of the consciousness level and the sleepiness level of the test subject, continuously indicates the sleepiness level between 0 (the maximum consciousness level) and 1 (the maximum sleepiness level). Thus, it is possible to directly evaluate the sleepiness level of the test subject by a value of the sleepiness level evaluation parameter.

According to another aspect of the invention, it is preferable that the consciousness level index band be set to have a bandwidth of ±0.05 Hz with respect to the conscious-state peak frequency as a center. By setting the consciousness level index band in such a manner as to have the bandwidth of 0.1 Hz like this, the consciousness level index band can precisely include the frequency components for indicating a consciousness state.

According to another aspect of the invention, it is preferable that the sleepiness level index band is set so as to include any frequency of 65 to 90% of the conscious-state peak frequency. From experimental result by many test subjects, it has been confirmed that a frequency component at a ratio of 65 to 90% with respect to the conscious-state peak frequency increases when sleepiness occurs. Therefore, if the sleepiness level index band is set so as to include any frequency of 65 to 90% of the conscious-state peak frequency, the sleepiness level index band can precisely include a frequency component corresponding to sleepiness.

According to another aspect of the invention, the evaluation means evaluates the sleepiness level of the test subject when the test subject operates the predetermined equipment. The evaluation means may repeatedly calculate the peak frequency of the spectrum signal, after the test subject starts operating the predetermined equipment. When the difference between the maximum peak frequency and the minimum peak frequency in a predetermined time period is equal to or less than a predetermined value, an average value of the peak frequencies in the time period may be set as the conscious-state peak frequency. When the test subject is in a state of tension or in a state of high sleepiness level, the intervals between the peaks of the heartbeat signal wander, or vary. Conversely, when variation in the peak frequencies of the spectrum signal is small, it is regarded that the test subject feels neither tension nor sleepiness. Therefore, an amount of variation in the peak frequencies may be judged by the difference between the maximum and minimum peak frequencies. The peak frequency at a time when the amount of variation is small may be set as the conscious-state peak frequency, in order to improve the precision of the conscious-state peak frequency.

According to another aspect of the invention, the evaluation means may calculate the conscious-state peak frequency every time the test subject starts operating the equipment. Also the evaluation means may determine a final conscious-state peak frequency on the basis of the latest conscious-state peak frequency and a past conscious-state peak frequency. This is because there is a case where the conscious-state peak frequency varies with a lapse of time.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

The following description of the preferred embodiments is merely exemplary in nature and is in no way intended to limit the invention, its application, or uses. An embodiment of a sleepiness level detection device according to the present invention will be hereinafter described with reference to the drawings. This embodiment explains a case in which the sleepiness level detection device installed in a vehicle detects a sleepiness of a driver during driving, but the sleepiness level detection device may be used for detecting the sleepiness of an operator or a watchman of equipment, which may be different from a vehicle.

Figure 1:
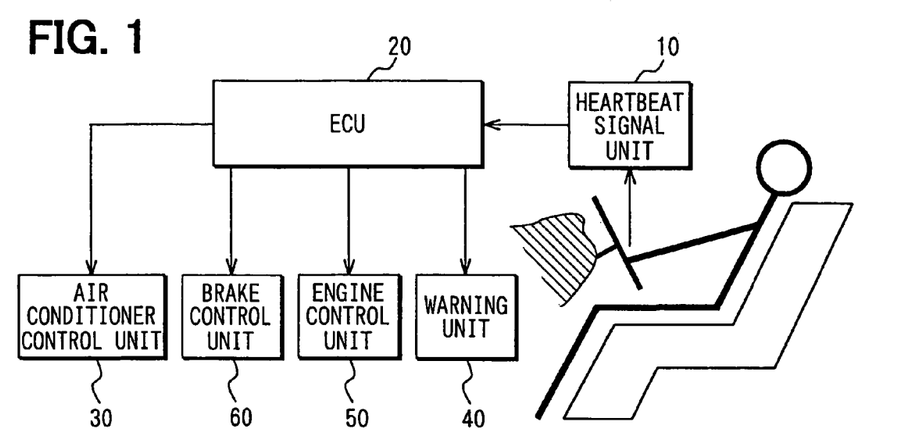
FIG. 1 is a block diagram of the schematic structure of a sleepiness level detection device according to an embodiment of the invention.

FIG. 1 is a block diagram which shows the schematic structure of the sleepiness level detection device according to this embodiment. Referring to FIG. 1, the sleepiness level detection device has a heartbeat signal detection unit 10 for detecting a heartbeat signal of a driver of a vehicle, and an ECU 20 for detecting the sleepiness level of the driver on the basis of the detected heartbeat signal. The ECU 20 is connected to an air conditioner control unit 30, a warning unit 40, an engine control unit 50, a brake control unit 60 and the like. Hence, in detecting that sleepiness occurs in the driver, the sleepiness level detection device (the ECU 20), in effect, clears the sleepiness out of the driver in accordance with the sleepiness level, and controls the vehicle to ensure overall safety.

The heartbeat signal detection unit 10 has a plurality of electrodes provided on a steering wheel. When each of the right and left hands of the driver makes contact with the electrode, a potential difference corresponding to the heart potential of the driver occurs between both electrodes. By successively detecting the potential difference occurring between both electrodes, the heartbeat signal of the driver is obtained.

Since the sleepiness level detection device is installed in the vehicle in this embodiment, the heartbeat signal detection unit 10 is composed of the electrodes provided on the steering wheel. The heartbeat signal, however, may be detected by other means. For example, a pulse wave sensor is usable as the other means for detecting the heartbeat signal. The pulse wave sensor has a couple of light emitting and receiving elements. The light emitting element irradiates the surface of the skin of the driver with light. Part of the light passes through the skin, and is dispersed by blood flowing through a blood vessel. Thus, an amount of light received by the light receiving element varies in accordance with an amount of blood flowing through the blood vessel. Therefore, also in the case of using the pulse wave sensor, it is possible to detect a signal corresponding with the movements of the heart of a driver, that is, a signal corresponding to the heartbeat signal.

It is preferable that the pulse wave sensor be used in such a manner that the light receiving element tightly makes contact with the surface of the skin of the driver, for the purpose of eliminating the effects of disturbance light. Therefore, the light receiving element of the pulse wave sensor may be provided in the steering wheel in a position suited for grip by the driver. Otherwise, as variously proposed, the pulse wave sensor in the shape of, for example, a wristwatch, a finger ring or the like may be put on the driver to detect the heartbeat signal (signal corresponding to the heartbeat signal).

Figure 2:
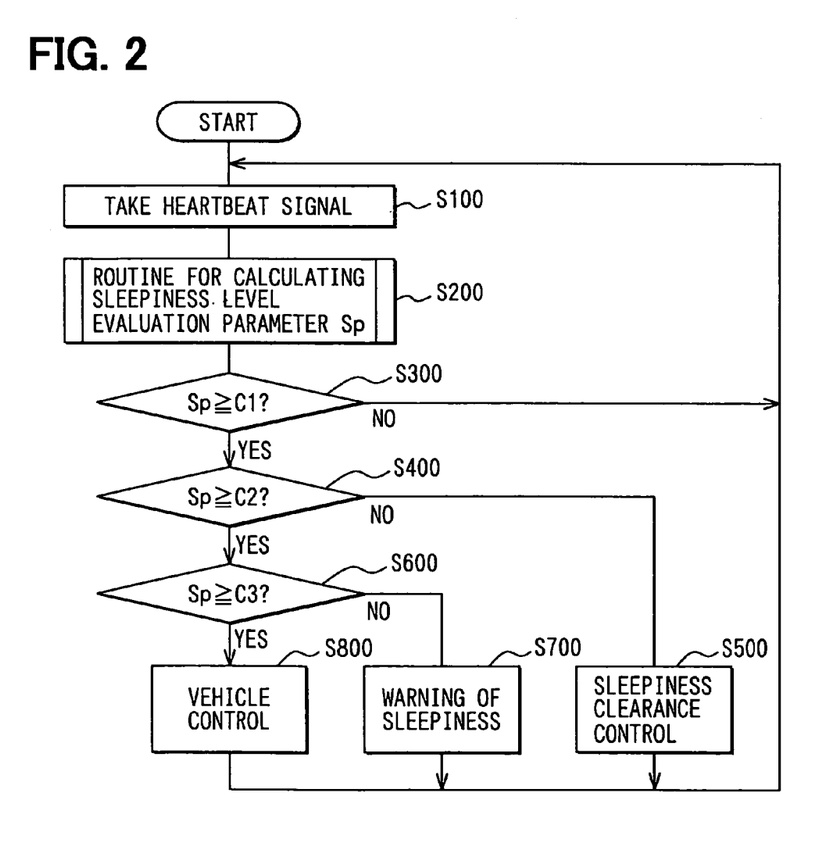
FIG. 2 is a flowchart of sleepiness level detection processing that is carried out by the sleepiness level detection device, and warning processing and the like, which is carried out when sleepiness is detected.

Then, sleepiness level detection processing, warning processing and the like will be described based on a flowchart of FIG. 2. The sleepiness level detection processing is carried out by the ECU 20. The warning processing is carried out when sleepiness is detected. First, the ECU 20 takes in the heartbeat signal outputted from the heartbeat signal detection unit 10 in step S100. In taking the heartbeat signal, the ECU 20 samples the heartbeat signal in a cycle of approximately 100 Hz, and converts an analog signal into a digital signal. A QRS wave of the heartbeat signal generally continues for approximately 0.1 second. Accordingly, the foregoing sampling in the cycle of approximately 100 Hz makes it possible to certainly take peak values of the heartbeat signal.

Then, in step S200, a sleepiness level evaluation parameter Sp for evaluating the sleepiness level of the driver is calculated on the basis of the taken heartbeat signal. A calculation method of the sleepiness level evaluation parameter Sp will be described later in detail.

After the sleepiness level evaluation parameter Sp is calculated in step S200, processing advances to step S300, and the sleepiness level evaluation parameter Sp is compared with the first criterion value C1. When the sleepiness level evaluation parameter Sp is judged to be smaller than the first criterion value C1 in this comparison, it is regarded that sleepiness does not occur in the driver, and hence the processing returns to step S100. When the sleepiness level evaluation parameter Sp is judged to be equal to or larger than the first criterion value C1 in step S300, on the other hand, the processing advances to step S400.

In step S400, the sleepiness level evaluation parameter Sp is further compared with the second criterion value C2, which is larger than the first criterion value C1. When the sleepiness level evaluation parameter Sp is judged to be smaller than the second criterion value C2, the sleepiness level of the driver is estimated to be low, the processing advances to step S500. In step S500, the ECU 20 outputs a control signal to the air conditioner control unit 30, to make the air conditioner control unit 30 carry out sleepiness improvement control. In sleepiness improvement control, cold air is blown on the driver by use of an air conditioner provided in the vehicle, or an aroma, having the effect of reducing sleepiness, is released from an outlet of the air conditioner. Therefore, if the level of sleepiness is low, sleepiness can be cleared by the sleepiness improvement control.

When the sleepiness level evaluation parameter Sp is judged to be equal to or larger than the second criterion value C2 in step S400, on the other hand, the processing advances to step S600. In step S600, the sleepiness level evaluation parameter Sp is compared with the third criterion value C3, which is larger than the second criterion value C2. When the sleepiness level evaluation parameter Sp is judged to be smaller than the third criterion value C3 in the judgment of step S600, the sleepiness level of the driver is estimated to be in a middle level. Thus, the ECU 20 outputs a warning signal to the warning unit 40 in step S700. The warning unit 40 issues a warning sound in relatively high volume or a warning message, to call attention to the driver. When the sleepiness level evaluation parameter Sp is judged to be equal to or larger than the third criterion value C3 in step S600, on the other hand, the sleepiness level of the driver is estimated to be high. In this case, the processing advances to step S800, and the ECU 20 output a control signal to the brake control unit 60 and/or the engine control unit 50, to make them carry out vehicle control. In vehicle control, the speed of the vehicle is reduced or the vehicle is stopped, by, for example, reducing the output of an engine or forcefully applying the brakes.

A sleepiness level evaluation parameter calculation routine, which is described above, will be hereinafter explained based on the flowchart of FIG. 3. First, in step S210, the heartbeat signal taken in step S100 of the flowchart of FIG. 2 is converted into a signal having peaks of R-waves.

Figure 4:
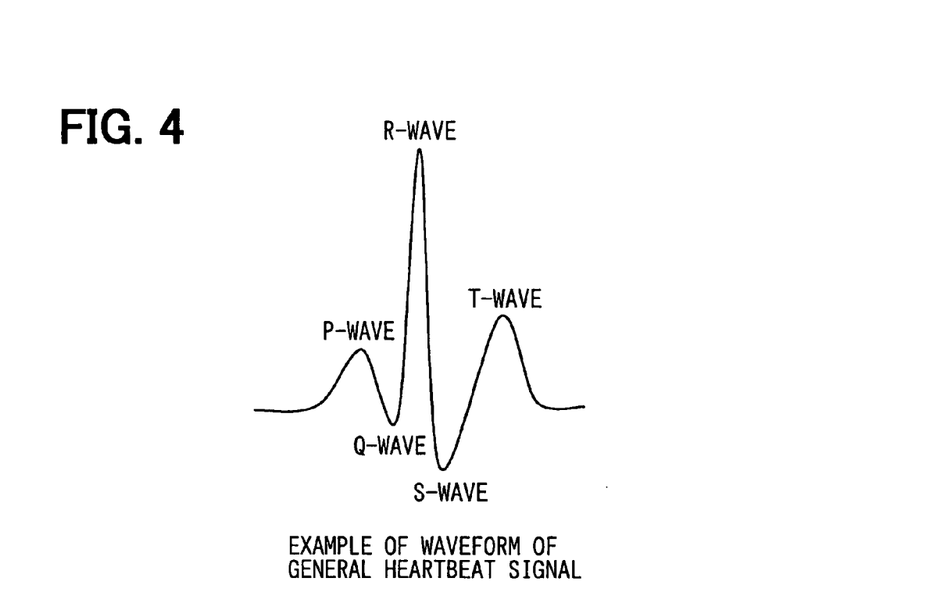
FIG. 4 is a waveform diagram of an example waveform of a general heartbeat signal.

FIG. 4 shows an example of a waveform of a general heartbeat signal. As shown in FIG. 4, the heartbeat signal includes a P-wave, a Q-wave, an R-wave, an S-wave, and a T-wave in a single waveform, and each wave shows a peak. Thus, if the heartbeat signal is subjected to direct frequency analysis, a spectrum signal including every frequency component described above is obtained. The sleepiness level detection device according to this embodiment, however, is to analyze a heart rate, in the heartbeat signal, per unit of time, in other words, to analyze the frequency components ascribable to the heart rate, so that the frequency components of every wave described above become a cause of an error. For this reason, as shown in FIG. 5, the heartbeat signal is converted into a signal having peaks of only the R-waves, which are the largest peaks of the heartbeat signal, and then the frequency analysis is carried out on the converted signal.

A unit of measuring time is 10 seconds in this embodiment. Every 10 seconds, the heartbeat signal sampled in the cycle of 100 Hz is converted as described above, and is subjected to frequency analysis by a fast Fourier transform (FFT) as described later, in order to obtain a spectrum signal which indicates the distribution of the frequency components included in the heartbeat signal.

If the heartbeat signal is sampled in a cycle of 100 Hz for 10 seconds, the number of samples is 1000(10(sec)×100 (Hz)). The frequency resolution of the spectrum signal obtained by FFT processing becomes low, with this sampling cycle and this number of samples. Thus, processing for improving the frequency resolution is carried out. In other words, when the heartbeat signal is sampled in the cycle of 100 Hz for ten seconds, the frequency resolution of the spectrum signal is 0.1 Hz (sampling cycle (100 Hz)/the number of sampling (1000)). Generally the heart rate is approximately 60 beats per minute, and a heartbeat frequency is 1 Hz, so that the frequency resolution of 0.1 Hz corresponds to a pretty high heart rate, that is, 6 beats.

Figure 5:
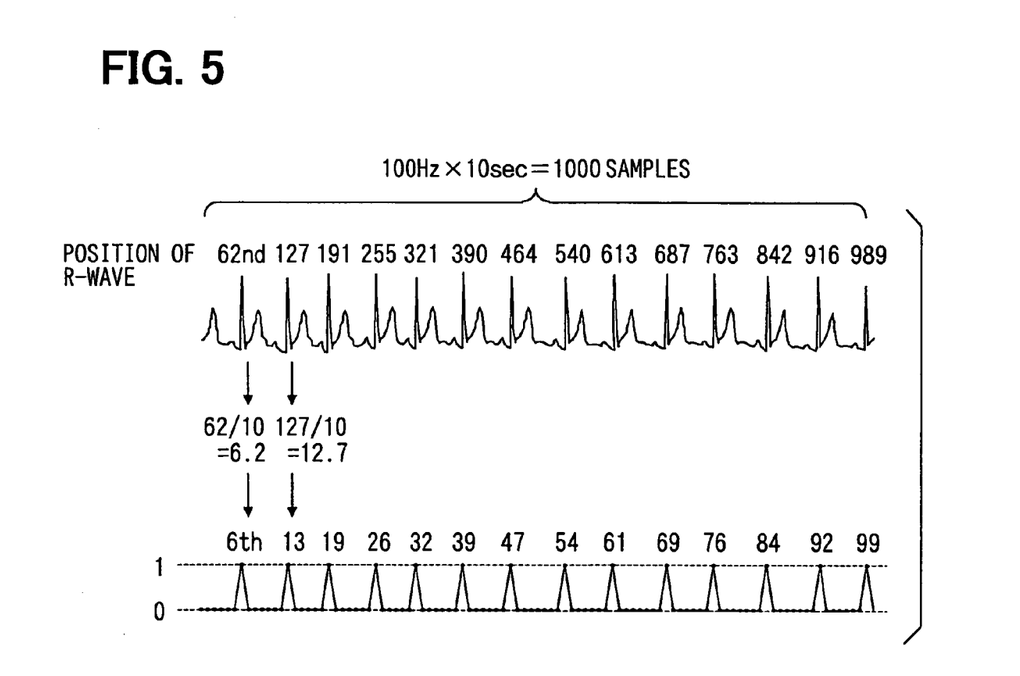
FIG. 5 is an explanatory view that explains a processing method for converting the heartbeat signal into a signal having peaks of only R-waves, which are the largest peaks of the heartbeat signal.

Therefore, as shown in FIG. 5, information (62, 127, . . . ) related to the positions of sampled R-waves is reduced by a factor of 10, to reduce the sampling frequency (from 100 Hz to 10 Hz). In this case, however, the number of sampling is also reduced by a factor of 10, and the frequency resolution is not improved, so that 924 dummy data (0 data) is added to the number of samplings. According to this processing, it is possible to improve the frequency resolution of the spectrum signal (increase the frequency resolution by a factor of approximately 10).

Figure 6:
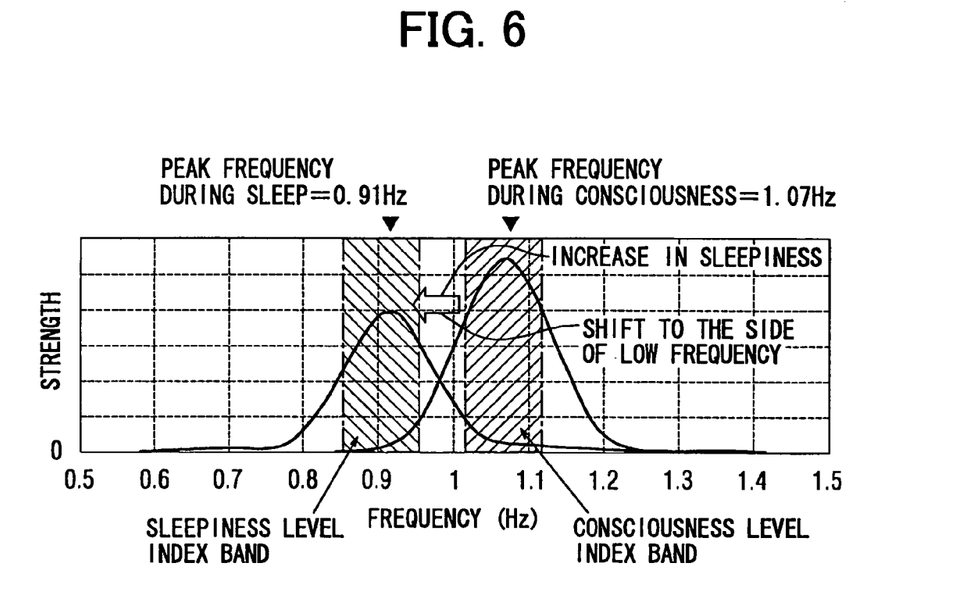
FIG. 6 is a characteristic graph of spectrum signals that indicate the distribution of frequency components of the heartbeat signal.

Then, in step S220, the FFT processing is performed on the converted signal calculated in step S210, to calculate the spectrum signal, which indicates the distribution of the frequency components in the heartbeat signal. FIG. 6 shows an example of calculated spectrum signals. As shown in FIG. 6, when a consciousness level of the driver is high, a spectrum signal having a peak in a relatively high frequency region is obtained. When the sleepiness level of the driver is high, a spectrum signal having a peak in a relatively low frequency region is obtained. This is because the frequency components included in the heartbeat signal of the driver decrease in accordance with an increase in the sleepiness level of the driver, because the heart rate decreases as the sleepiness of the driver increases.

Then, the length of elapsed time since the driver begins driving the vehicle is judged in step S230. When the elapsed time is shorter than T1 in this judgment, and it is judged that the driving has just started, the processing of this routine ends. When it is judged that the elapsed time is equal to or longer than T1 and equal to or shorter than T2, a conscious-state peak frequency of the driver is detected in step S240. Then, in step S250, a consciousness level index band α and a sleepiness level index band β are set on the basis of the conscious-state peak frequency. When the elapsed time is judged to be longer than T2, the processing of steps S260 to S280 is performed, to calculate the sleepiness level evaluation parameter Sp, which indicates the sleepiness level of the driver.

Figure 7:
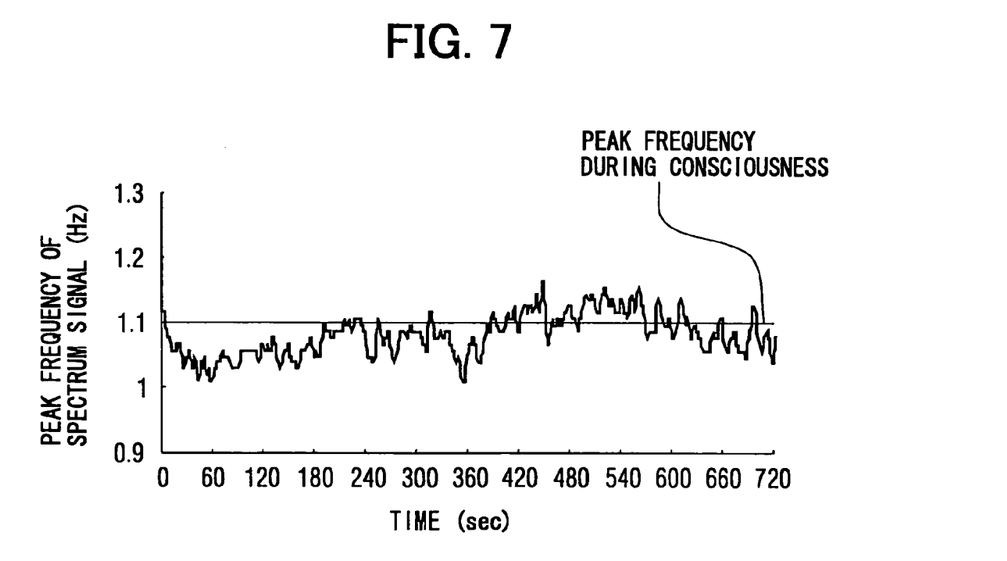
FIG. 7 is a graph of variation in a peak frequency of the spectrum signal from when a driver starts driving a vehicle.

A reason why a different processing is carried out, as described above, in accordance with the elapsed time since the beginning of driving will be hereinafter described. FIG. 7 is a graph showing a variation in a peak frequency of a spectrum signal, which is obtained by subjecting a heartbeat signal to the FFT processing, from when a driver begins driving a vehicle. As shown in FIG. 7, the peak frequency detected just after the start of driving is largely different from a normal peak frequency in a state in which the driver feels neither tension nor sleepiness (hereinafter called "conscious-state peak frequency"). The detected peak frequency tends to approach the conscious-state peak frequency with a lapse of time. As to this point, the inventor of the present application verified whether or not other drivers have a similar tendency. The result of verification is shown in a graph of FIG. 8.

Figure 8:
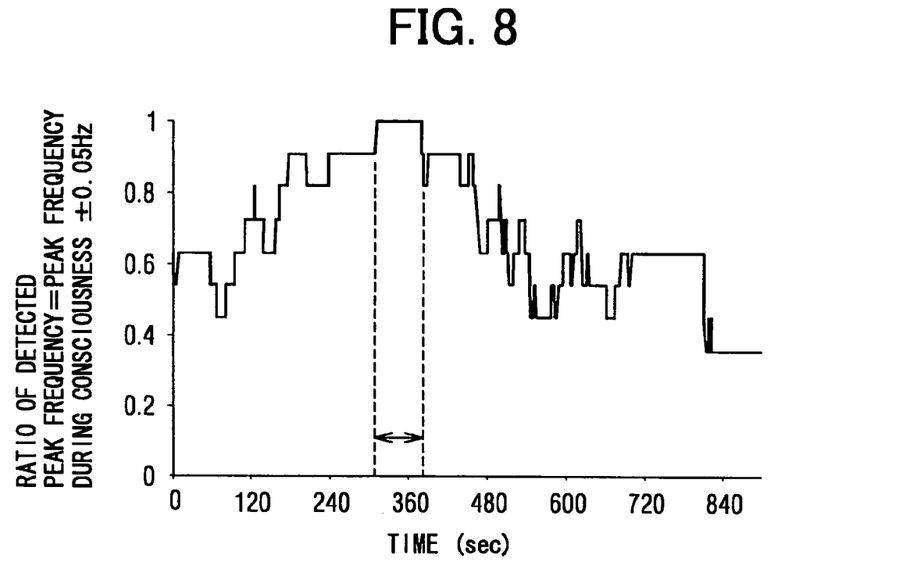
FIG. 8 is a graph that shows the ratio of drivers whose detected peak frequencies are different from their conscious-state peak frequencies according to time periods since the start of driving.

FIG. 8 shows the ratio of the drivers, whose detected peak frequencies are different from their conscious-state peak frequencies in a range equal to or less than a predetermined value (±0.05 Hz), of the whole of drivers who are the targets of the verification, according to time periods since the start of driving. As shown in FIG. 8, the ratio of the drivers, whose detected peak frequencies are largely different from their conscious-state peak frequencies, is large from just after the start of driving to approximately 100 seconds. However, the ratio of drivers, whose detected peak frequencies are close to their conscious-state peak frequencies, gradually increases at a point in time after 100 seconds. For instance, the difference between the detected peak frequency and the conscious-state peak frequency becomes slight in every driver between 300 seconds and 400 seconds. The ratio of the drivers, whose detected peak frequencies are slightly different from their conscious-state peak frequencies, remains large until approximately 500 seconds. However, the ratio of the drivers, whose detected peak frequencies are largely different from their conscious-state peak frequencies, increases after 500 seconds.

According to the foregoing result of verification, it is apparent that the peak frequency of the spectrum signal detected in a time period between a lapse of T1 (100 seconds, and preferably 300 seconds) and a lapse of T2 (500 seconds, and preferably 400 seconds), not just after the start of driving, approximates the conscious-state peak frequency of each driver. Therefore, in this embodiment, when the elapsed time since the start of driving is equal to or longer than T1 and equal to or shorter than T2, the processing advances to step S240. The peak frequency of the spectrum signal calculated in step S220 is extracted and estimated as the conscious-state peak frequency of the driver. It is preferable that T1 and T2 are set so that the spectrum signal is calculated for a plurality of times in the time difference between T1 and T2. In step S240, it is preferable that the peak frequency of each spectrum signal is extracted, and the plurality of peak frequencies are averaged to estimate an averaged peak frequency as the conscious-state peak frequency.

Furthermore, the conscious-state peak frequency calculated in the past may be stored. The latest and past conscious-state peak frequencies may be averaged with or without a weight, to update the conscious-state peak frequency. In this case, the conscious-state peak frequency is estimated with high precision on the basis of the peak frequencies over a long time period. If the difference between the stored conscious-state peak frequency and the latest conscious-state peak frequency is equal to or more than a predetermined value, a warning pertaining to an abnormality of the physical condition of the driver may be issued. Furthermore, in consideration of a case in which multiple drivers drive, for example, a number of switches or the like may be provided to distinguish between the drivers, and the foregoing conscious-state peak frequencies may be stored for each driver.

In the continuous step S250, the consciousness level index band $\alpha$ and the sleepiness level index band $\beta$ are set on the basis of the conscious-state peak frequency estimated in step S240. The consciousness level index band $\alpha$ is set to have a bandwidth of ±0.05 Hz with respect to the estimated conscious-state peak frequency. Taking the case of FIG. 6, for example, since a conscious-state peak frequency is estimated at 1.07 Hz, a consciousness level index band $\alpha$ has a lower limit frequency of 1.02 Hz and an upper limit frequency of 1.12 Hz. Since the consciousness level index band $\alpha$ includes the conscious-state peak frequency, the strength of the spectrum signal belonging to the consciousness level index band $\alpha$ becomes high, when the consciousness level of the driver is high. In other words, the strength of the spectrum signal in the consciousness level index band $\alpha$ is an index to the consciousness level of the driver.

A setup of the sleepiness level index band $\beta$ will be described. As described above, since the heart rate of the driver decreases as the sleepiness level of the driver increases, the peak of the spectrum signal, which indicates the distribution of the frequency components of the heartbeat signal, moves toward the low frequency side. The inventor of the present application carried out the following measurements to specify a frequency band which most precisely indicates the sleepiness level of each driver.

Figure 9:
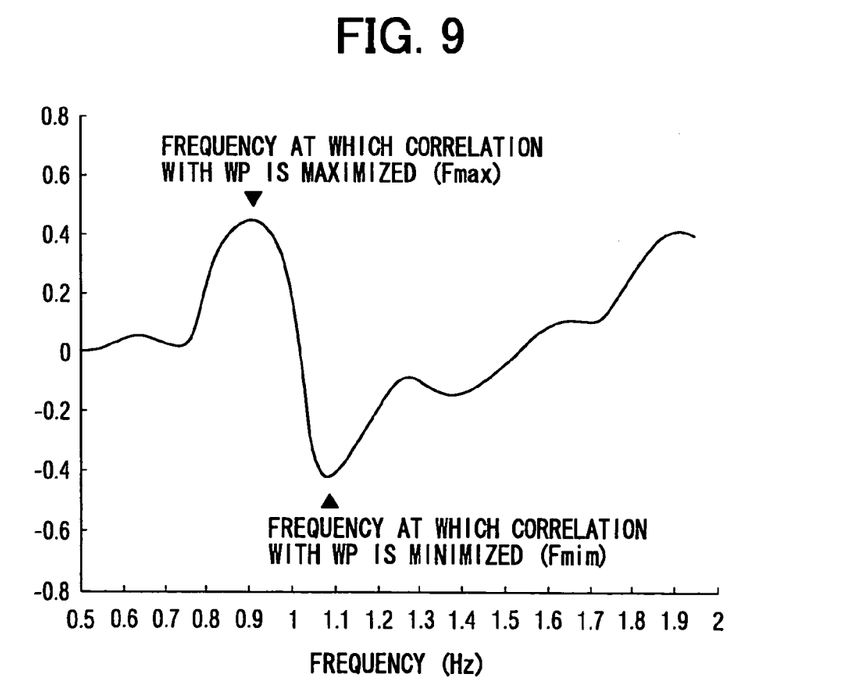
FIG. 9 is a graph of the correlation between variation in an amount of transverse deviation of the vehicle (that is, variation in work performance (WP)) and variation in the signal strength of each frequency of the spectrum signal.

First, the inventor had a number of drivers operate a drive simulator and measured the amount of transverse deviation of a vehicle during the operation. The amount of the transverse deviation, referred to as work performance (WP), was used as an objective index of the sleepiness level of the driver. Furthermore, the heartbeat signal of the driver was measured at the same time, and the heartbeat signal was subjected to the FFT processing to calculate a spectrum signal. The correlation between variation in an amount of transverse deviation of the vehicle (that is, variation in the WP) and variation in signal strength in each frequency of the spectrum signal was investigated. FIG. 9 shows the result of the investigation. FIG. 9 is a graph of the correlation between variation in an amount of transverse deviation of the vehicle (that is, variation in work performance (WP)) and variation in the signal strength of each frequency of the spectrum signal.

Referring to FIG. 9, a correlation coefficient with the WP is minimized at a conscious-state peak frequency (Fmin). This means that the signal strength of the conscious-state peak frequency decreases when the amount of transverse deviation becomes large (the WP is small), and the signal strength of the conscious-state peak frequency increases when the amount of transverse deviation becomes small (the WP is large).

In an example shown in FIG. 9, contrary to the conscious-state peak frequency (Fmin), the correlation coefficient with the WP is maximized at a frequency (Fmax) of approximately 0.91 Hz. The sleepiness level index band $\beta$ is set to have a predetermined bandwidth with respect to 0.91 Hz, and hence the strength of the spectrum signal belonging to the sleepiness level index band $\beta$ is an index of the sleepiness level of the driver.

Figure 10:
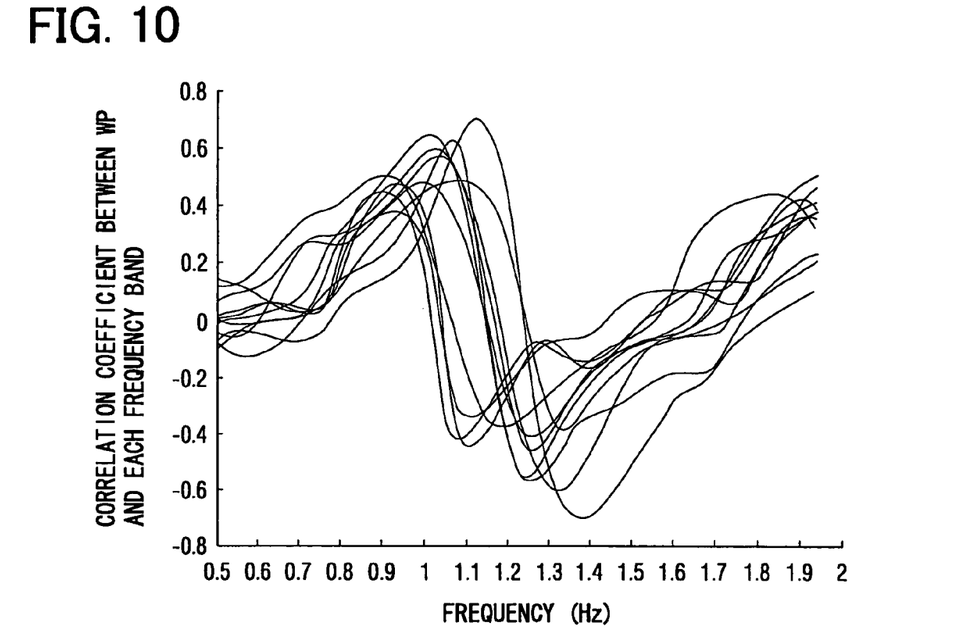
FIG. 10 is a graph of the correlation coefficient between WP and each frequency band, and the frequency of a number of drivers.

Investigating the foregoing correlation between the WP and the signal strength in each frequency of the spectrum signal with respect to the plurality of drivers, as shown in FIG. 10, it is apparent that the frequency (Fmax), at which the correlation coefficient with the WP reaches its maximum, widely varies (1.03±0.12 Hz). Thus, if a certain band is simply set as the sleepiness level index band $\beta$, the precision in the index of the sleepiness level widely varies from driver to driver. FIG. 10 is a graph of the characteristic curves of a number of drivers, each curve indicating the correlation between variation in an amount of transverse deviation of the vehicle and variation in the signal strength of each frequency of the spectrum signal.

Figure 11:
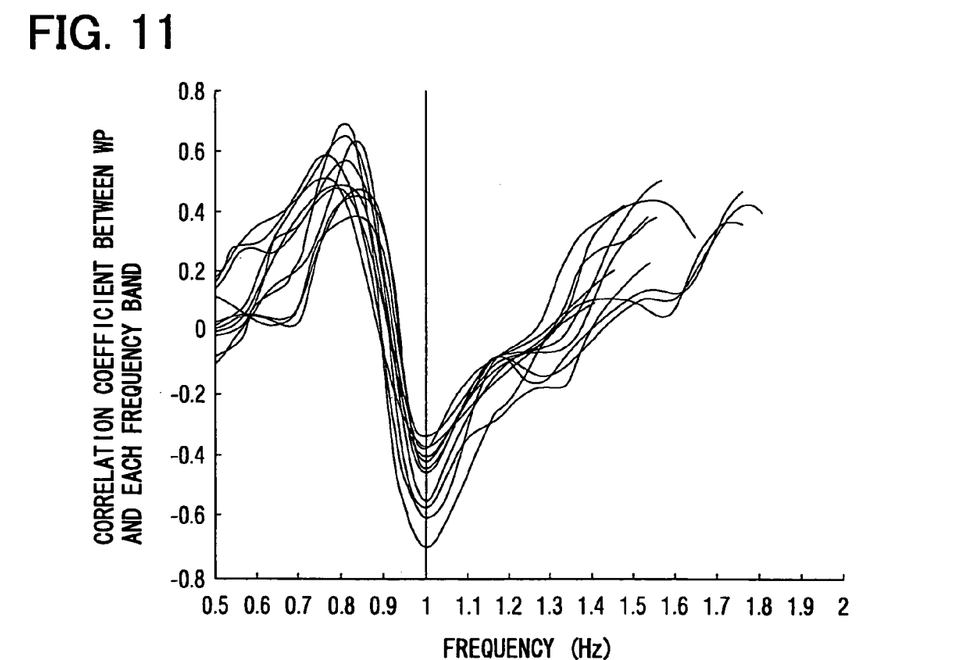
FIG. 11 is a graph of the range of variations of a frequency (Fmax), at which the correlation with the WP becomes largest, when the conscious-state peak frequency (Fmin) of each driver is normalized at 1 Hz.

To directly obtain the frequency (Fmax), at which the correlation with the WP becomes maximum, as described above, it is necessary to measure the WP. In other words, a system for measuring only the heartbeat signal, like this embodiment, cannot directly obtain the frequency (Fmax), at which the correlation with the WP reaches its maximum. Therefore, it is necessary to indirectly obtain the frequency (Fmax), at which the correlation with the WP is maximized, with high precision by the measurable heartbeat signal. For the purpose of this, the inventor of the present application investigated the range of variations of the frequency (Fmax), at which the correlation with the WP becomes maximum, when the conscious-state peak frequency (Fmin) of each driver was normalized at 1 Hz. In this case, it became apparent that the range of variations of the frequency (Fmax), at which the correlation with the WP is maximized, became narrow. In an example of FIG. 11, every frequency (Fmax) at which the correlation with the WP is maximized belongs to a range of 0.83±0.03 Hz.

Therefore, the frequency at a predetermined ratio of the conscious-state peak frequency is set as the foregoing frequency (Fmax), at which the correlation with the WP is maximized. Then, a frequency band with respect to the frequency is set as the sleepiness level index band β.

Figure 12:
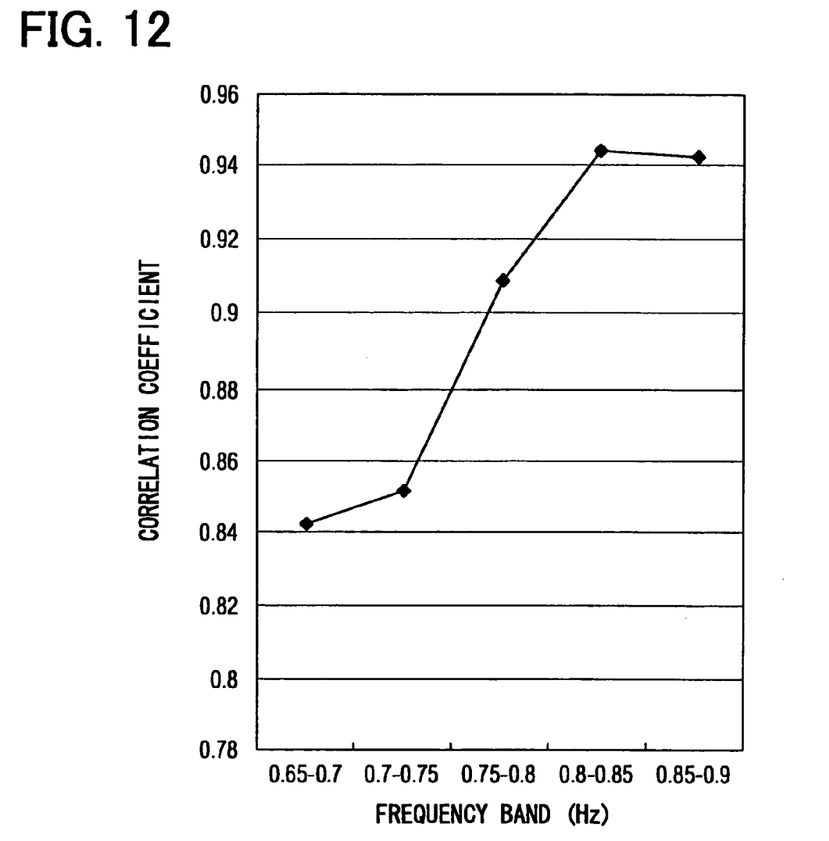
FIG. 12 is a graph of the correlation between the strength of the spectrum signal belonging to each frequency band and the WP, when the conscious-state peak frequency (Fmin) is normalized at 1 Hz.
Figure 13:
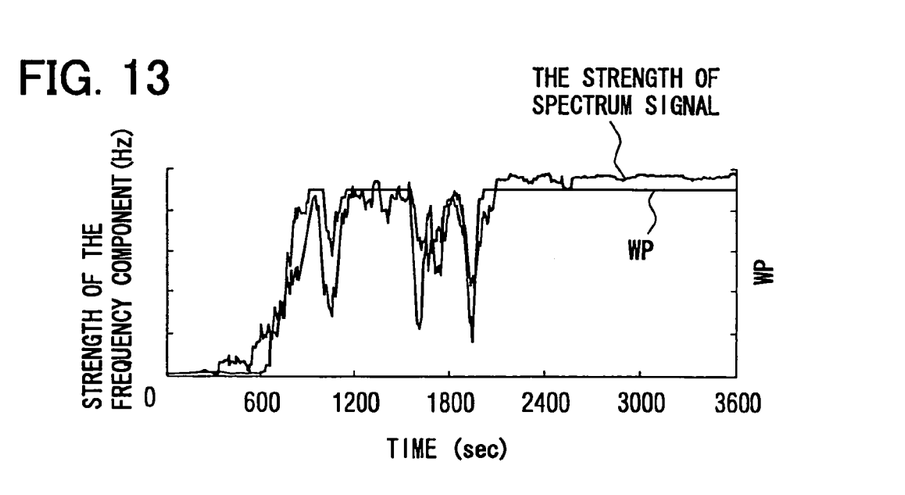
FIG. 13 is a time chart of variation in the strength of the spectrum signal belonging to the frequency band of 0.80 to 0.85 Hz, and variation in the WP.

FIG. 12 shows the correlation between the strength of spectrum signals belonging to each frequency band (0.65 to 0.70 Hz, 0.70 to 0.75 Hz, 0.75 to 0.80 Hz, 0.80 to 0.85 Hz, and 0.85 to 0.90 Hz) and the WP, when the conscious-state peak frequency (Fmin) is normalized at 1 Hz. Even the correlation between the strength of the spectrum signal belonging to the frequency band of 0.65 to 0.70 Hz and the WP exceeds 0.84. Especially in the frequency bands of 0.75 to 0.90 Hz, the correlation with the WP exceeds 0.9, and the correlation with the WP is maximized at the frequency band of 0.80 to 0.85 Hz. FIG. 13 is a time chart that shows variation in the strength of the spectrum signal belonging to the frequency band of 0.80 to 0.85 Hz, and variation in the WP. It is apparent from FIG. 13, that both of the strength and the WP have the almost same tendency in variation.

Based on the results of FIGS. 12 and 13, a value in a range of 65 to 90%, preferably 75 to 90% and further preferably 80 to 85% is used as the predetermined ratio for calculating the frequency (Fmax), at which the correlation with the WP is maximized, by the conscious-state peak frequency (Fmin). Thus, it is possible to precisely obtain the frequency (Fmax), at which the correlation with the WP is maximized. After the frequency (Fmax), at which the correlation with the WP is maximized is calculated, in this manner, a frequency band having a bandwidth of ±0.05 Hz with respect to this frequency is set as the sleepiness level index band β. The sleepiness level index band β may be set in such a manner that the upper and lower limit frequencies of the sleepiness level index band β are calculated by multiplying the upper and lower limit frequencies of the consciousness level index band α by the predetermined ratio, respectively.

Figure 3:
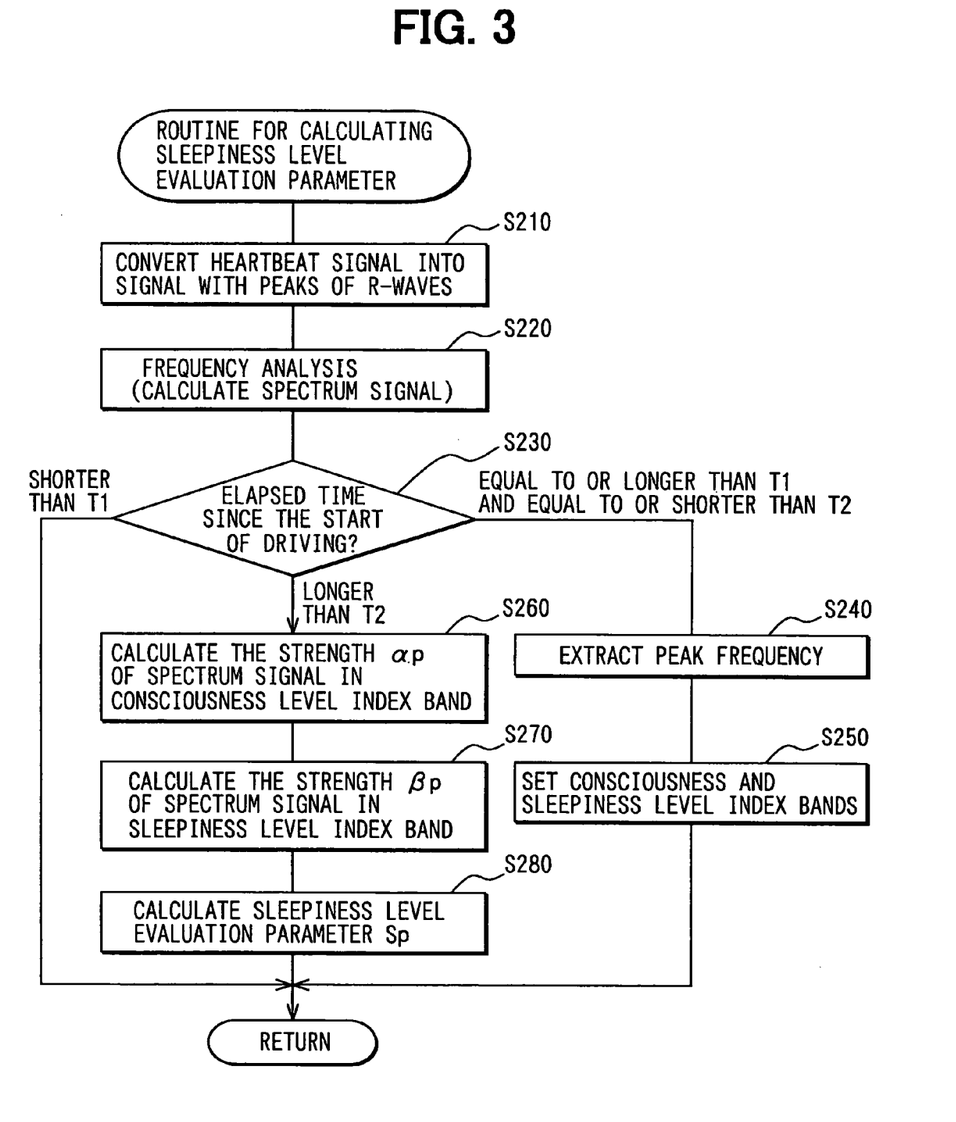
FIG. 3 is a flowchart of a calculation routine of a sleepiness level evaluation parameter.

Referring to the flowchart of FIG. 3, when the elapsed time since the start of driving is judged to be longer than T2 in step S230, the processing advances to step S260, in order to calculate the strength αp of a spectrum signal belonging to the consciousness level index band α set as described above. Then, the strength βp of a spectrum signal belonging to the sleepiness level index band β is calculated in step S270. Then, in step S280, the sleepiness level evaluation parameter Sp is calculated with the following equation.

$$Sp = \beta p / (\alpha p + \beta p)$$

The sleepiness level evaluation parameter Sp calculated with this equation considers both of the consciousness level and the sleepiness of the driver. The sleepiness level evaluation parameter Sp continuously indicates the sleepiness level between 0 (the maximum consciousness level) and 1 (the maximum sleepiness level). Thus, it is possible to directly evaluate the sleepiness level of the driver by a value of the sleepiness level evaluation parameter Sp.

The preferred embodiment of the present invention has been described above. The sleepiness level detection device according to the present invention, however, is not limited to the foregoing embodiment, and various modifications are applicable thereto.

In the foregoing embodiment, for example, the sleepiness level evaluation parameter Sp is calculated by the strength αp and βp of the spectrum signals, which belong to the consciousness level index band α and the sleepiness level index band β. The sleepiness level of the driver may be detected on the basis of only the strength βp of the spectrum signal, which belongs to the sleepiness level index band β. When the consciousness level of the driver is high, the heartbeat hardly decreases. The low frequency component included in the heartbeat signal is slight, and hence the strength βp of the spectrum signal belonging to the sleepiness degree index band β becomes low. As the sleepiness level of the driver increases, on the other hand, a decrease in the heart rate becomes conspicuous, and the low frequency component included in the heartbeat signal increases. Thus, the strength βp of the spectrum signal in the sleepiness level index band β increases. Since the strength βp of the spectrum signal in the sleepiness level index band β correlates with the sleepiness level, it is possible to detect the sleepiness level of the driver only by the strength βp of the spectrum signal, which belongs to the sleepiness level index band β.

In the foregoing embodiment, the consciousness level index band α and the sleepiness level index band β have the bandwidth of 0.1 Hz, but the bandwidth thereof is not limited to 0.1 Hz. Furthermore, in the foregoing embodiment, the peak frequency of the spectrum signal detected in a time period, in which time equal to or longer than T1 and equal to or shorter than T2 has been elapsed from the time the driver begins driving, is estimated as the conscious-state peak frequency. The peak frequencies of the spectrum signal, however, may be repeatedly calculated after the driver starts driving. When the difference between the maximum and minimum values of the peak frequency in a predetermined time period is equal to or less than a predetermined value, an average value of the peak frequency in the time period may be set as the conscious-state peak frequency. When the driver is in a state of tension or sleepiness, the intervals between the peaks of the heartbeat signal wander, or change. Conversely, when variation in the peak frequency of the spectrum signal is small, it is regarded that the driver feels neither tension nor sleepiness. Therefore, an amount of variation in the peak frequency may be judged by the difference between its maximum and minimum values. When the amount of variation is small, the peak frequency may be set as the conscious-state peak frequency.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A sleepiness level detection device comprising:
   means for detecting a heartbeat signal of a test subject;
   calculation means for performing frequency analysis on the heartbeat signal and calculating a spectrum signal that indicates the distribution of frequency components included in the heartbeat signal; and
   evaluation means for settling a band having a lower frequency than a conscious-state peak frequency as a sleepiness level index band for indicating a sleepiness level, in the spectrum signal, with respect to the conscious-state peak frequency in a conscious state of the test subject, and evaluating the sleepiness level of the test subject, on basis of strength of the spectrum signal in the sleepiness level index band; wherein the evaluation means evaluates the sleepiness level of the test subject when the test subject operates predetermined equipment, and the peak frequency of the spectrum signal, at a time after a predetermined time has elapsed since the fully awake test subject began operating the predetermined equipment, is set as the conscious-state peak frequency.

2. The sleepiness level detection device according to claim 1, wherein
the calculation means converts the heartbeat signal into a signal that has peaks only at largest peak positions of the heartbeat signal, and performs frequency analysis on the converted signal.

3. The sleepiness level detection device according to claim 1, wherein
the evaluation means selects the predetermined time in a range from 100 seconds to 500 seconds.

4. The sleepiness level detection device according to claim 1, wherein
the evaluation means calculates the conscious-state peak frequency every time the test subject starts operating the equipment, and the evaluation means determines a final conscious-state peak frequency based on a latest conscious-state peak frequency and a past conscious-state peak frequency.

5. A sleepiness level detection device comprising:
means for detecting a heartbeat signal of a test subject;
calculation means for performing frequency analysis on the heartbeat signal and calculating a spectrum signal that indicates the distribution of frequency components included in the heartbeat signal; and
evaluation means for settling a band having a lower frequency than a conscious-state peak frequency as a sleepiness level index band for indicating a sleepiness level, in the spectrum signal, with respect to the conscious-state peak frequency in a conscious state of the test subject, and evaluating the sleepiness level of the test subject, on basis of strength of the spectrum signal in the sleepiness level index band; wherein
the evaluation means calculates the conscious-state peak frequency is by averaging peak frequencies of a plurality of spectrum signals that are calculated for a predetermined detection time, from a point in time after a predetermined time has elapsed since the test subject began operating predetermined equipment.

6. A sleepiness level detection device comprising:
means for detecting a heartbeat signal of a test subject;
calculation means for performing frequency analysis on the heartbeat signal and calculating a spectrum signal that indicates the distribution of frequency components included in the heartbeat signal; and
evaluation means for settling a band having a lower frequency than a conscious-state peak frequency as a sleepiness level index band for indicating a sleepiness level, in the spectrum signal, with respect to the conscious-state peak frequency in a conscious state of the test subject, and evaluating the sleepiness level of the test subject, on basis of strength of the spectrum signal in the sleepiness level index band; wherein
the evaluation means sets a band including the conscious-state peak frequency as a consciousness level index band, and evaluates the sleepiness level of the test subject by using strength of the spectrum signals in the consciousness level index band and the sleepiness level index band.

7. The sleepiness level detection device according to claim 6, wherein
the evaluation means calculates a sleepiness level evaluation parameter, a denominator of the sleepiness level evaluation parameter is a sum of the strength of the spectrum signals in the consciousness and sleepiness level index bands, and a numerator of the sleepiness level evaluation parameter is a the strength of the spectrum signal in the sleepiness level index band.

8. The sleepiness level detection device according to claim 6, wherein
the consciousness level index band is set to have a bandwidth of ±0.05 Hz with respect to the conscious-state peak frequency as a center.

9. The sleepiness level detection device according to claim 6, wherein
the sleepiness level index band is set to include any frequency of 65 to 90% of the conscious-state peak frequency.

10. A sleepiness level detection device comprising:
means for detecting a heartbeat signal of a test subject;
calculation means for performing frequency analysis on the heartbeat signal and calculating a spectrum signal that indicates the distribution of frequency components included in the heartbeat signal; and
evaluation means for settling a band having a lower frequency than a conscious-state peak frequency as a sleepiness level index band for indicating a sleepiness level, in the spectrum signal, with respect to the conscious-state peak frequency in a conscious state of the test subject, and evaluating the sleepiness level of the test subject, on basis of strength of the spectrum signal in the sleepiness level index
the evaluation means evaluates the sleepiness level of the test subject, when the test subject operates predetermined equipment, and the evaluation means repeatedly calculates a peak frequency of the spectrum signal after the test subject starts operating the predetermined equipment, and when the difference between maximum peak frequency and minimum peak frequency in a predetermined time period is equal to or less than a predetermined value, an average value of the peak frequencies in the time period is set as the conscious-state peak frequency.

* * * * *